US00PP26270P2

(12) United States Plant Patent
Kanaya et al.

(10) Patent No.: US PP26,270 P2
(45) Date of Patent: Dec. 22, 2015

(54) ***CALIBRACHOA* PLANT NAMED 'SUNBEL 871'**

(50) Latin Name: ***Calibrachoa* sp.**
Varietal Denomination: Sunbel 871

(71) Applicants: Takeshi Kanaya, Chiba (JP); Kiyoshi Miyazaki, Shiga (JP); Yasuyuki Murakami, Shiga (JP)

(72) Inventors: Takeshi Kanaya, Chiba (JP); Kiyoshi Miyazaki, Shiga (JP); Yasuyuki Murakami, Shiga (JP)

(73) Assignee: Suntory Flowers LTD., Tokyo (JP)

( * ) Notice: Subject to any disclaimer, the term of this patent is extended or adjusted under 35 U.S.C. 154(b) by 207 days.

(21) Appl. No.: 13/998,604

(22) Filed: Nov. 15, 2013

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — June Hwu
(74) *Attorney, Agent, or Firm* — C. A. Whealy

(57) ABSTRACT

A new and distinct cultivar of *Calibrachoa* plant named 'Sunbel 871', characterized by its compact and mounding plant habit; vigorous growth habit; freely branching habit; early and freely flowering habit; long flowering period; red purple-colored flowers with yellow-colored throats; and good garden performance.

1 Drawing Sheet

Botanical designation: *Calibrachoa* sp.
Cultivar denomination: 'SUNBEL 871'.

BACKGROUND OF THE INVENTION

The present invention relates to a new and distinct cultivar of *Calibrachoa* plant, botanically known as *Calibrachoa* sp. and hereinafter referred to by the name 'Sunbel 871'.

The new *Calibrachoa* plant is a product of a planned breeding program conducted by the Inventors in Higashiomi, Shiga, Japan. The objective of the breeding program is to develop new compact, mounding and freely branching *Calibrachoa* plants with numerous large and attractive flowers.

The new *Calibrachoa* plant originated from a cross-pollination conducted by the Inventors in Higashiomi, Shiga, Japan in June, 2010 of a proprietary selection of *Calibrachoa* sp. identified as code number 10C204, not patented, as the female, or seed, parent with a proprietary selection of *Calibrachoa* sp. identified as code number 8739-1, not patented, as the male, or pollen, parent. The new *Calibrachoa* plant was discovered and selected by the Inventors as a single flowering plant from within the progeny of the stated cross-pollination in a controlled greenhouse environment in Higashiomi, Shiga, Japan in August, 2011.

Asexual reproduction of the new *Calibrachoa* plant by vegetative cuttings in a controlled greenhouse environment in Higashiomi, Shiga, Japan since August, 2011 has shown that the unique features of this new *Calibrachoa* plant are stable and reproduced true to type in successive generations.

SUMMARY OF THE INVENTION

Plants of the new *Calibrachoa* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunbel 871'. These characteristics in combination distinguish 'Sunbel 871' as a new and distinct *Calibrachoa* plant:

1. Compact and mounding plant habit.
2. Vigorous growth habit.
3. Freely branching habit.
4. Early and freely flowering habit.
5. Long flowering period.
6. Red purple-colored flowers with yellow-colored throats.
7. Good garden performance.

Plants of the new *Calibrachoa* can be compared to plants of the female parent selection. Plants of the new *Calibrachoa* differ primarily from plants of the female parent selection in the following characteristics:

1. Plants of the new *Calibrachoa* have larger flowers than plants of the female parent selection.
2. Plants of the new *Calibrachoa* and the female parent selection differ in flower color as plants of the female parent selection have bright red-colored flowers.

Plants of the new *Calibrachoa* can be compared to plants of the male parent selection. Plants of the new *Calibrachoa* differ primarily from plants of the male parent selection in flower color as plants of the male parent selection have dark orange red-colored flowers.

Plants of the new *Calibrachoa* can also be compared to plants of *Calibrachoa* sp. 'Suncalred', disclosed in U.S. Plant Pat. No. 23,831. In side-by-side comparisons conducted in Higashiomi, Shiga, Japan, plants of the new *Calibrachoa* and 'Suncalred' differed primarily in the following characteristics:

1. Plants of the new *Calibrachoa* had spatulate-shaped leaves whereas plants of 'Suncalred' have narrowly elliptic-shaped leaves.
2. Plants of the new *Calibrachoa* flowered earlier than plants of 'Suncalred'.

3. Plants of the new *Calibrachoa* and 'Suncalred' differed in flower color as plants of 'Suncalred' had red-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Sunbel 871' grown in a container.

The photograph at the bottom of the sheet is a close-up view of a typical flowering plant of 'Sunbel 871'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial *Calibrachoa* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Calibrachoa* sp. 'Sunbel 871'.

Parentage:

*Female, or seed, parent.*—Proprietary selection of *Calibrachoa* sp. identified as code number 10C204, not patented.

*Male, or pollen, parent.*—Proprietary selection of *Calibrachoa* sp. identified as code number 8739-1, not patented.

Propagation:

*Type.*—By vegetative cuttings.

*Time to initiate roots, summer.*—About one week at temperatures about 15° C. to 20° C.

*Time to produce a rooted young plant, summer.*—About three weeks at temperatures about 15° C. to 20° C.

*Root description.*—Fibrous; white in color.

*Rooting habit.*—Freely branching.

Plant description:

*Plant and growth habit.*—Compact and mounding plant habit; freely branching habit with numerous lateral branches developing per plant; pinching enhances lateral branch development; vigorous growth habit.

*Plant height.*—About 19.8 cm.

*Plant diameter.*—About 47.3 cm.

Lateral branch description:

*Length.*—About 21.5 cm.

*Diameter.*—About 2 mm.

*Internode length.*—About 1.84 cm.

*Strength.*—Strong.

*Aspect.*—Upright to outwardly.

*Texture.*—Densely pubescent.

*Color.*—Close to 144A.

Leaf description:

*Arrangement.*—Alternate, simple.

*Length.*—About 3 cm.

*Width.*—About 1.17 cm.

*Shape.*—Spatulate.

*Apex.*—Obtuse.

*Base.*—Cuneate.

*Margin.*—Entire.

*Texture, upper and lower surfaces.*—Pubescent.

*Venation pattern.*—Pinnate; reticulate.

*Color.*—Developing and fully expanded leaves, upper surface: Close to 137A; venation, close to 143C. Developing and fully expanded leaves, lower surface: Close to 137C; venation, close to 144D.

*Petioles.*—Length: About 2.5 mm. Diameter: About 1.6 mm. Texture, upper and lower surfaces: Pubescent. Color, upper and lower surfaces: Close to 143C.

Flower description:

*Flower arrangement and habit.*—Single salverform flowers arising from upper leaf axils; freely flowering habit with usually about 127 flowers developing per plant; flowers face upright or outwardly.

*Fragrance.*—None detected.

*Natural flowering season.*—Early flowering habit, plants of the new *Calibrachoa* initiate and develop flowers about three to four weeks after planting; long flowering period, flowering naturally commences during the early spring and plants flower continuously throughout the summer until late autumn in Japan.

*Flower longevity.*—Individual flowers last about seven to ten days on the plant; flowers not persistent.

*Flower diameter.*—About 2.5 cm.

*Flower length (depth).*—About 2.21 cm.

*Throat diameter.*—About 6.7 mm.

*Tube length.*—About 1.49 cm.

*Tube diameter, base.*—About 2.4 mm.

*Flower buds.*—Shape: Cylindrical. Length: About 1.72 cm. Diameter: About 3.7 mm. Color: Close to 79C.

*Corolla.*—Arrangement: Five petals fused at the base and opening into a flared trumpet. Petal length from throat: About 1 cm. Petal width: About 1.13 cm. Petal shape: Roughly spatulate. Petal apex: Cuspidate. Petal margin: Entire. Petal texture, upper and lower surfaces: Smooth, glabrous. Throat texture: Smooth, glabrous. Tube texture: Pubescent. Color: Petal, when opening, upper surface: Close to 59B; towards the throat, close to N79A. Petal, when opening, lower surface: Close to 64B to 64C. Petal, fully opened, upper surface: Close to 59B; towards the throat, close to N79A; venation, close to N79A, faint. Petal, fully opened, lower surface: Close to N66C to N66D; venation, close to N66C to N66D. Throat: Close to 12A; venation, close to 146B. Tube: Close to 12C; venation, close to 187A.

*Calyx.*—Arrangement: One star-shaped tubular calyx tube with five sepals fused at the base. Sepal length: About 6.8 mm to 9.7 mm. Sepal width: About 2.5 mm. Sepal shape: Lanceolate. Sepal apex: Obtuse. Sepal margin: Entire. Sepal texture, upper and lower surfaces: Pubescent. Sepal color: Immature and mature, upper surface: Close to 138A. Immature and mature, lower surface: Close to 138B.

*Peduncles.*—Length: About 1.32 cm. Diameter: About 1 mm. Angle: Upright to outwardly. Strength: Strong. Texture: Pubescent. Color: Close to 138B.

*Reproductive organs.*—Stamens: Quantity: Five per flower. Stamen length: About 8.2 mm to 11 mm. Anther shape: Ellipsoidal. Anther size: About 1.5 mm by 1.8 mm. Anther color: Close to 8B. Pollen amount: Moderate. Pollen color: Close to 8B. Pistils: Quantity: One per flower. Pistil length: About 1.07 cm. Style color: Close to 144D. Stigma shape: Transversely ellipsoidal. Stigma color: Close to 144C. Ovary color: Close to 144A.

*Seeds and fruits.*—Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen & pest resistance: Plants of the new *Calibrachoa* have not been observed to be resistant to pests and pathogens common to *Calibrachoa* plants.

It is claimed:

1. A new and distinct *Calibrachoa* plant named 'Sunbel 871' as illustrated and described.

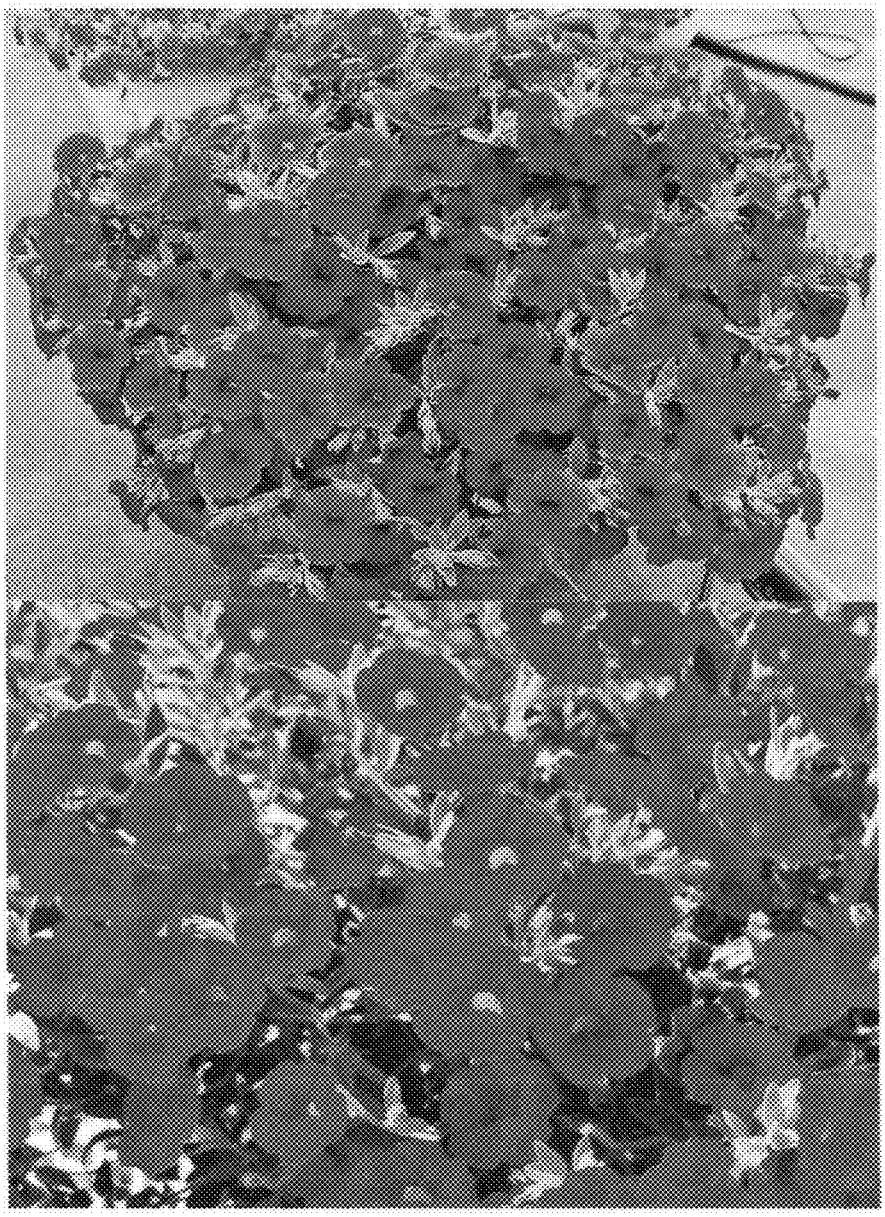

* * * * *